(12) United States Patent
Holzmayer et al.

(10) Patent No.: US 8,907,828 B2
(45) Date of Patent: Dec. 9, 2014

(54) METHOD AND DEVICE FOR TESTING THE MATERIAL OF A TEST OBJECT IN A NONDESTRUCTIVE MANNER

(75) Inventors: Bernhard Holzmayer, Hohenstein (DE); Michael Halter, Pfullingen (DE)

(73) Assignee: Institut Dr. Foerster GmbH & Co. KG, Reutlingen (DE)

( * ) Notice: Subject to any disclaimer, the term of this patent is extended or adjusted under 35 U.S.C. 154(b) by 0 days.

(21) Appl. No.: 14/232,991

(22) PCT Filed: Jul. 18, 2012

(86) PCT No.: PCT/EP2012/064057
§ 371 (c)(1),
(2), (4) Date: Jan. 15, 2014

(87) PCT Pub. No.: WO2013/011050
PCT Pub. Date: Jan. 24, 2013

(65) Prior Publication Data
US 2014/0152483 A1 Jun. 5, 2014

(30) Foreign Application Priority Data
Jul. 19, 2011 (DE) .......................... 10 2011 079 438

(51) Int. Cl.
*H03M 1/10* (2006.01)
*H03M 1/60* (2006.01)
*G01N 27/90* (2006.01)

(52) U.S. Cl.
CPC ............. *H03M 1/60* (2013.01); *G01N 27/9006* (2013.01)
USPC ........... 341/120; 341/121; 341/141; 341/142; 341/157; 341/162

(58) Field of Classification Search
USPC .......... 341/120, 121, 139, 140, 157, 176, 181
See application file for complete search history.

(56) References Cited

U.S. PATENT DOCUMENTS

| 4,445,088 | A | 4/1984 | Schuebel |
| 5,329,281 | A * | 7/1994 | Baumgartner et al. ....... 341/139 |
| 6,275,781 | B1 | 8/2001 | Maness et al. |
| 6,556,859 | B1 * | 4/2003 | Wohlgemuth et al. ........ 600/509 |
| 6,633,822 | B2 * | 10/2003 | Maness et al. .................. 702/56 |
| 6,760,623 | B2 * | 7/2004 | Stahmann et al. ................ 607/9 |

(Continued)

FOREIGN PATENT DOCUMENTS

WO 2006007826 A1 1/2006

*Primary Examiner* — Linh Nguyen
(74) *Attorney, Agent, or Firm* — Duane Morris LLP

(57) ABSTRACT

A method for testing the material of a test object (8) in a nondestructive manner, said test object being moved relative to a probe (1) at a variable relative speed, comprises the following steps: detecting a probe signal (US) by means of the probe (1), subjecting the probe signal (US) to analog-to-digital conversion in order to generate a digitized probe signal (USD) in the form of a sequence of digital words with a predefined, in particular constant, word repetition rate, n-stage decimation of the word repetition rate of the digitized probe signal (USD) or of a digital demodulation signal (UM) derived from the digitized probe signal by means of n cascaded decimation stages (5_1 to 5_n), where n≥2, selecting an output signal (UA_1 to UA_n) of one of the n decimation stages (5_1 to 5_n) depending on the instantaneous relative speed and filtering the selected output signal by means of a digital filter (7), which is clocked with the word repetition rate of the selected output signal.

9 Claims, 1 Drawing Sheet

(56) References Cited

U.S. PATENT DOCUMENTS

Figure 1:
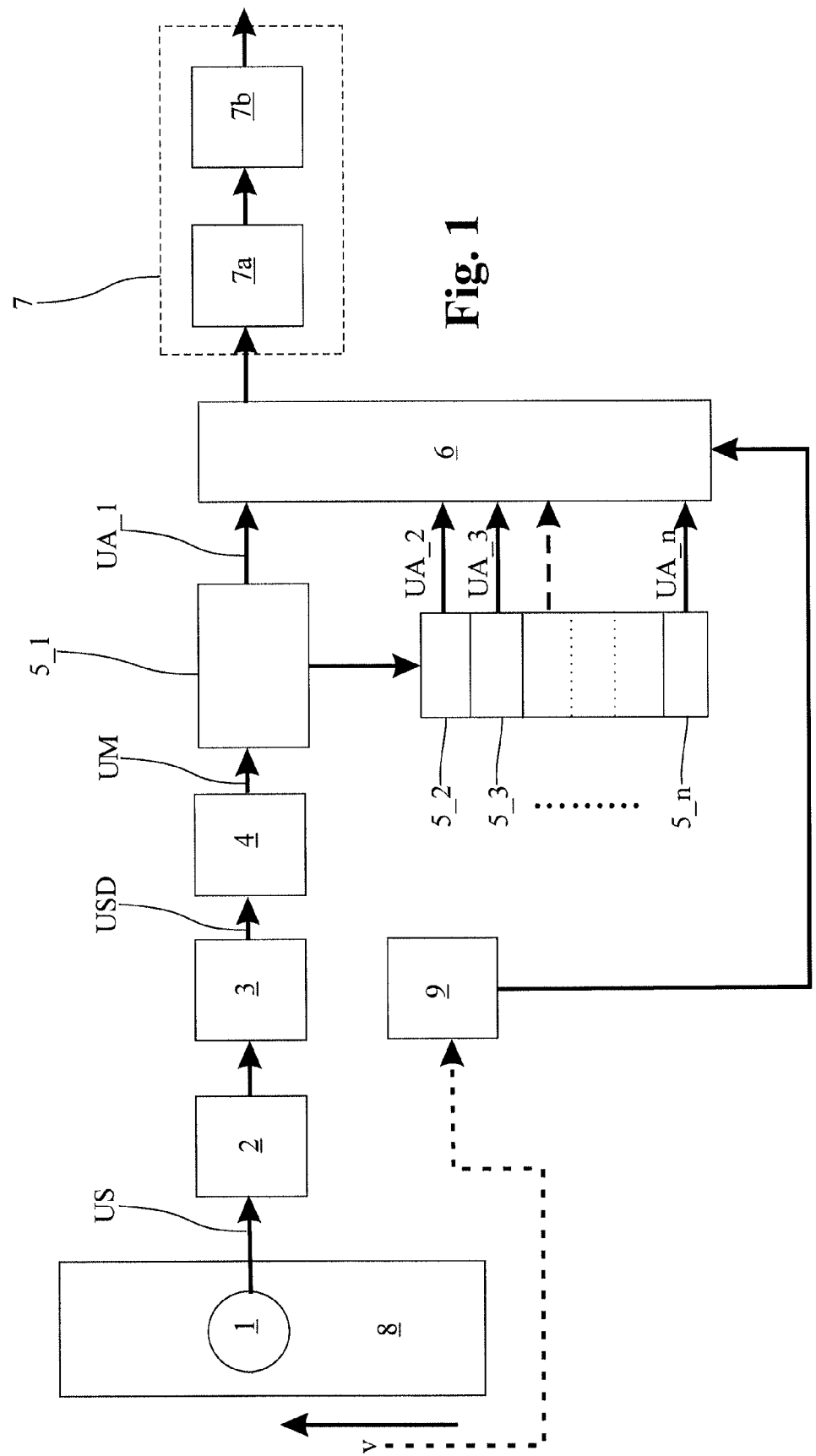

| | | |
|---|---|---|
| 6,868,348 B1 * | 3/2005 | Stoutenburg et al. ............ 702/56 |
| 7,317,415 B2 * | 1/2008 | Kaiser ............................ 341/155 |
| 7,474,247 B1 * | 1/2009 | Heinks et al. ................. 341/155 |
| 7,623,053 B2 * | 11/2009 | Terry et al. .................... 341/143 |
| 7,942,817 B2 * | 5/2011 | Zhang et al. ................... 600/300 |
| 8,237,601 B2 * | 8/2012 | Dunbar et al. ................. 341/176 |
| 8,803,723 B2 * | 8/2014 | Venkataraman et al. ...... 341/155 |
| 2003/0227288 A1 | 12/2003 | Lopez |
| 2004/0066189 A1 | 4/2004 | Lopez |
| 2007/0080681 A1 | 4/2007 | Hoelzl et al. |
| 2007/0208262 A1 * | 9/2007 | Kovacs ......................... 600/509 |
| 2007/0242758 A1 | 10/2007 | Hoelzl et al. |
| 2010/0090877 A1 * | 4/2010 | Dunbar et al. ................ 341/176 |
| 2012/0010508 A1 | 1/2012 | Sokulin et al. |

\* cited by examiner

METHOD AND DEVICE FOR TESTING THE MATERIAL OF A TEST OBJECT IN A NONDESTRUCTIVE MANNER

The invention relates to a method and a device for testing the material of a test object in a nondestructive manner.

Nondestructive material testing involves detecting faults in a test object, for example in the form of a metallic semifinished product.

One test method variant involves applying periodic alternating electromagnetic fields to the test object by means of a sinusoidally energized transmitting coil. The eddy currents thereby induced in the test object in turn induce in a probe, for example in the form of a coil or coil arrangement, a periodic electrical signal having a carrier oscillation, the amplitude and/or phase of which is modulated in a characteristic manner by a fault in the test object if a fault reaches a measurement range of the probe.

During the material testing, the test object can be moved relative to the probe at a variable relative speed, for example if the test object is accelerated or decelerated relative to the probe. The spectrum of a signal brought about in the probe on account of a fault in the test object depends on the relative speed, and so relative-speed-dependent filter sets are usually required for the probe signal, which entails an additional outlay.

The same correspondingly applies to test method variants in which a carrier signal is not applied to the test object, since a spectrum of the probe signal is dependent on the relative speed in those variants, too.

WO 2006/007826 A1 discloses a method for nondestructively and contactlessly detecting faults in a test object moved relative to a probe at a variable relative speed, wherein periodic alternating electromagnetic fields are applied to the test object by means of a transmitter and a periodic electrical signal is detected by means of the probe, said signal having a carrier oscillation, the amplitude and/or phase of which is modulated by a fault in the test object, wherein an A/D converter stage is triggered with an n-th, integral fraction of a frequency of a carrier oscillation, where n is chosen, inter alia, depending on the relative speed.

The problem addressed by the invention is that of providing a method and a device for testing the material of a test object in a nondestructive manner which enable reliable and easily implementable material testing at variable relative speeds between test object and probe.

The invention solves this problem by means of a method as claimed in claim 1 and a device as claimed in claim 7.

The method for testing the material of a test object in a nondestructive manner, said test object being moved relative to a probe at a variable relative speed, comprises the following steps: detecting a probe signal, for example a probe current and/or a probe voltage, by means of the probe, subjecting the probe signal to analog-to-digital conversion in order to generate a digitized probe signal in the form of a sequence of digital words with a predefined, in particular constant, word repetition rate, n-stage decimation of the word repetition rate of the digitized probe signal or of a digital demodulation signal derived from the digitized probe signal by means of n cascaded decimation stages, where n≥2, a respective decimation stage outputting a digital output signal having a reduced word repetition rate, for example reduced by one (1) octave, but a constant word width, selecting the output signal of one of the n decimation stages depending on the instantaneous relative speed, and filtering the selected output signal by means of a digital filter, which is clocked with the word repetition rate of the selected output signal.

The realization of digital filters is all the more problematic, the greater the separation between a filter cut-off frequency and a sample or word repetition rate (required word widths, instabilities, etc.). According to the invention, therefore, the word repetition rate is decreased as much as possible before filtering. The decreased word repetition rate can correspond, for example, approximately to 20 to 30 times the maximum signal frequency that occurs. In applications with a fluctuating relative speed, a fluctuating signal frequency is present. This circumstance necessitates adapting the cut-off frequencies of the filter or filters to the signal frequency during operation. Changing the filter cut-off frequency by reloading filter coefficients in the course of operation is problematic (transient effects, checking stability of all coefficient sets, etc.).

Since, in digital filters, the cut-off frequency is in a fixed ratio to the sample or word repetition rate, according to the invention the sample or word repetition rate used is instead adapted dynamically to the instantaneous signal frequency, i.e. relative speed. The coefficient sets of the filter can then remain unchanged.

In one embodiment, the n-stage decimation of the word repetition rate comprises the following steps: decimating the word repetition rate in one of the decimation stages, in particular the first decimation stage, by an settable factor k, where ≥2, preferably 20≤k≤40, and decimating the word repetition rate in the remaining decimation stages, in particular the second n-th decimation stages, in each case by a constant factor of two, i.e. exactly one octave. In this way, it is possible to run through a large dynamic range in a finely stepped manner. Preferably, k is set depending on the instantaneous relative speed.

In one embodiment, the digital filter is a bandpass filter, in particular having predefined filter coefficients that are constant during operation, i.e. during the process of testing the material of the test object in a nondestructive manner.

In one embodiment, the word repetition rate of the digitized probe signal or of the digital demodulation signal lies in a range of 1 kHz to 200 MHz, in particular 2 MHz to 6 MHz.

In one embodiment, the method furthermore comprises the following steps: applying an alternating magnetic field to the test object in order to generate a corresponding resulting alternating magnetic field in the test object, the alternating magnetic field changing periodically with at least one predefined carrier frequency, such that the probe signal has the at least one carrier frequency and is modulated in terms of its amplitude and/or phase depending on material properties of the test object, and digitally demodulating the digitized probe signal by multiplying the digitized probe signal by a digitized carrier signal having the at least one carrier frequency, in order to generate the digitized demodulation signal in the form of a sequence of digital words with the predefined word repetition rate of the analog-to-digital conversion.

The device is designed for carrying out the method and comprises the probe, an analog-to-digital converter designed for subjecting the probe signal to analog-to-digital conversion in order to generate the digitized probe signal, the n cascaded decimation stages, selection means, for example a switching matrix or a multiplexer, designed for selecting the output signal of one of the n decimation stages depending on the relative speed, and the digital filter.

In one embodiment, the probe is a magnetic field probe designed, in particular, for detecting a magnetic field inductively or by using the Hall effect.

In one embodiment, provision is made of: magnetic field generating means designed for applying the alternating magnetic field to the test object, and a digital demodulator designed for digitally demodulating the digitized probe signal.

The invention is described below with reference to the drawing, which illustrates preferred embodiments of the invention. In this case, in a schematic fashion:

FIG. 1 shows a device for testing the material of a test object in a nondestructive manner.

FIG. 1 shows a device for testing the material of a test object 8 in a nondestructive manner, said test object being moved relative to a magnetic field probe 1 at a variable relative speed, which is known in the device, and an alternating magnetic field being applied to said test object by means of magnetic field generating means (not illustrated more specifically), said alternating magnetic field being generated by means of an excitation signal, the excitation signal and thus also the alternating magnetic field changing periodically with at least one predefined excitation or carrier frequency. The excitation or carrier frequency can lie, for example, in a range of 1 kHz to 500 kHz.

As a result, a corresponding active or resulting alternating magnetic field is generated in the test object, such that a probe signal US has the at least one carrier frequency and is modulated in terms of its amplitude and/or phase depending on material properties of the test object.

The probe signal US is filtered by means of an anti-aliasing (AAL) filter 2 connected downstream and is then subjected to analog-to-digital conversion by means of an analog-to-digital converter 3 in order to generate a digitized probe signal USD in the form of a sequence of digital words with a predefined, constant word repetition rate and a predefined, constant word width. The probe signal US is thus digitized in a time- and amplitude-discrete manner with a constant word repetition or sample rate. The word repetition rate is determined by the analog-to-digital converter 3 and is 4 Msamples/s, by way of example. The analog-to-digital converter 3 and the upstream circuitry in the form of the anti-aliasing filter 2 provide for compliance with Shannon's theorem, i.e. the input signal of the analog-to-digital converter 3 contains only frequency components<2 MHz.

A digital demodulator 4 serves for digitally demodulating the digitized probe signal USD by multiplying the digitized probe signal USD by a digitized carrier signal (not illustrated more specifically) having the at least one carrier frequency, in order to generate a digitized demodulation signal UM in the form of a sequence of digital words with the predefined word repetition rate. The demodulation is effected in a phase-locked manner with the excitation signal in order that the phase shift between excitation signal and probe signal US can be determined, which contains testing information. The demodulation is effected by multiplication by the excitation signal whilst maintaining the full word repetition rate of the analog-to-digital converter 3.

The demodulation can be performed twice, namely firstly as multiplication by a cosine signal having the carrier frequency in order to generate an X-component and as multiplication by a sine signal having the carrier frequency in order to generate a Y-component. These multiplications give rise to the sum and the difference of the present spectrum with the carrier frequency. The further processing of the two demodulated components takes place in an identical manner in each case, the further processing being described below by way of example only for one component.

Conventionally, the demodulation is effected by means of 1 or 2 samples per carrier period at fixed phase angles. In this case, the demodulation simultaneously means sampling at the carrier frequency or double the carrier frequency. In order to avoid disturbances as a result of aliasing products, before this demodulation it is necessary to suppress frequency ranges at 0 Hz and around the carrier frequency and the multiples thereof by means of an anti-aliasing filter.

According to the invention, the demodulation is effected with the full, constant word repetition rate of the analog-to-digital converter 3, such that the demodulation is independent of the excitation or carrier frequency. This reduces an analog circuit outlay upstream of the analog-to-digital converter 3 to a minimum, namely a constant AAL low-pass filter at half the word repetition rate or word repetition frequency of the analog-to-digital converter 3. By virtue of the fact that the word repetition rate is not reduced before and during the demodulation, no AAL filter is required before the demodulation.

A decimator having n cascaded decimation stages 5_1 to 5_n serves for the n-stage decimation of the word repetition rate of the digital demodulation signal UM, outputs of the respective decimation stages 5_1 to 5_n being connected to corresponding inputs of a selection means in the form of a switching matrix 6. The number n of decimation stages can be 13, for example.

A low-pass filter (not shown) is provided in the demodulator 4 or in a manner connected downstream, said low-pass filter being dimensioned in such a way that secondary demodulation products at double the carrier frequency are sufficiently suppressed. At the same time, the filter serves as an AAL filter before the decimation of the word repetition rate.

An output of the switching matrix 6 is connected to a digital bandpass filter 7 as application filter, the switching matrix 6 selecting a decimation stage depending on the instantaneous relative speed, which is made available to the switching matrix 6 by a speed measuring device 9. The output signal selected by means of the switching matrix 6 serves as input signal for the bandpass filter 7, which is clocked with the correspondingly reduced word repetition rate of the selected output signal.

On account of the relative-speed-dependent clocking of the bandpass filter 7, the cut-off frequencies thereof arise automatically appropriately with respect to the instantaneous relative speed, such that the relative-speed-dependent spectrum of the signal generated in the probe 1 is automatically taken into account, without this necessitating relative-speed-dependent filter sets, as are required conventionally.

The bandpass filter or application filter 7, comprising a low-pass filter 7a and a high-pass filter 7b, substantially serves for application-specific interference suppression. Interference to be filtered arises principally from the test material, for example on account of microstructure changes, permeability fluctuations, surface roughness, etc. The high-pass filter 7b is of importance for this. The low-pass filter 7a serves for low-frequency interference suppression, for example for suppressing power supply system hum, etc.

The passband of the application filter 7 corresponds to the frequencies of the different material faults to be found at a given track speed (narrow crack crossed perpendicularly to wide crack crossed obliquely). A correspondingly bandpass-filtered demodulation signal is output at an output of the application filter 7, which demodulation signal can be evaluated, for example, if appropriate after a further word repetition rate reduction, in a microprocessor and/or dedicated hardware for identifying faults in the test object.

In applications with a fluctuating track or relative speed, a fluctuating signal frequency is present. This circumstance necessitates adapting the cut-off frequencies of the application filter or application filters to the signal frequency during operation. However, changing the filter cut-off frequency by reloading the coefficients in the course of operation is problematic (transient effects, checking the stability of all coefficient sets, etc.). However, since, in digital filters, the cut-off frequency is in a fixed ratio to the clock frequency, i.e. word repetition rate, the clock frequency is instead adapted dynamically to the signal frequency. The coefficient sets of the application filter 7 can then remain unchanged during operation.

The bandwidth must be adjustable depending on the material faults that occur, on the one hand, and the occurrence of interference signals, on the other hand. While the low-pass filter 7a of the application filter 7 is always operated with the same coefficient set, a plurality of application-specific coefficient sets can be kept available for the high-pass filter 7b of the application filter 7 and can be selected in an application-specific manner by an operator in a set-up phase. During the operation of the test device, however, it is not necessary to alter a coefficient set.

The realization of the application filter 7 is all the more complex, the greater the separation between a filter cut-off frequency and the clock frequency of the application filter 7. On account of the decimator, in this regard an optimized clock frequency, i.e. word repetition rate, is always made available. The word repetition rate can be decimated by means of the decimator for example to 24 times the maximum signal frequency to be expected.

The decimation is not carried out in one step, but rather divided into a first decimation stage 5_1, which varies the word repetition rate within one octave, and decimation stages 5_2 to 5_n which in each case halve the word repetition rate in a chain.

The chain of the decimation or halving stages 5_2 to 5_n provides a tap after each stage. That means that the signals are available simultaneously in octave steps in many detection frequencies. In the event of changes in the signal frequency, it is possible to change to a different, associated tap by means of the switching matrix 6. The dynamic range over which a change can be carried out can become as large as desired, in principle, by the chain of the halving stages 5_2 to 5_n being lengthened.

Each of the decimation stages 5_1 to 5_n has a decimation filter (not shown) with a small separation between cut-off frequency and associated word repetition rate, such that the decimation filters can be realized in a simple and stable manner.

The first decimation stage 5_1 reduces from the word repetition rate of the analog-to-digital converter 3 to the highest required detection frequency with a decimation rate k that is variable over one octave, where k is 20, 21, 22 . . . 40, for example. The rate reduction can be produced, for example, by the removal of the next k−1 samples after a sample. By means of the first decimation stage 5_1, the word repetition rate can be varied for example in 20 stages over one octave with a step size<=5%.

A variation of k takes place in a manner adapted to the signal frequency, which is in turn detected by way of the relative speed. In the case of a fluctuating relative speed, speed measurement values are regularly detected, and the rate reduction k is incorporated dynamically during operation.

The variation range of the word repetition rate is extended beyond one octave by means of the decimation stages 5_2 to 5_n as far as the lowest required word repetition rate. The rate reduction by the factor of 2 arises as a result of every second sample being omitted.

The chain of the decimation stages 5_2 to 5_n is always operated according to the minimum signal frequency over the entire length. The tap for the further processing of the test signal can be effected after each halving stage. The decimator itself in this case always remains unchanged.

It goes without saying that the demodulator can be dispensed with in the case of unmodulated probe signals.

The embodiments shown enable reliable and easily implementable material testing at variable relative speeds between test object and probe.

What is claimed is:

1. A method for testing the material of a test object (8) in a nondestructive manner, said test object being moved relative to a probe (1), at a variable relative speed, comprising the following steps:
   detecting a probe signal (US) by means of the probe
   subjecting the probe signal (US) to analog-to-digital conversion in order to generate a digitized probe signal (USD) in the form of a sequence of digital words with a predefined, in particular constant, word repetition rate,
   n-stage decimation of the word repetition rate of the digitized probe signal (USD) or of a digital demodulation signal (UM) derived from the digitized probe signal, wherein the n-stage decimation is performed by means of n cascaded decimation stages (5_1 to 5_n), where n≥2,
   selecting an output signal (UA_1 to UA_n) of one of the n decimation stages (5_1 to 5_n) depending on the instantaneous relative speed, and
   filtering the selected output signal by means of a digital filter (7), which clocked with the word repetition rate of the selected output signal.

2. The method as claimed in claim 1, characterized in that the n-stage decimation of the word repetition rate comprises the following steps:
   decimating the word repetition rate in one of the decimation stages, in particular the first decimation stage (5_1), by a settable factor k, where k≥2, preferably 20≤k ≤40, and
   decimating the word repetition rate in the remaining decimation stages, in particular the second to n-th decimation states (5_2 to 5_n), by a constant factor of two.

3. Method as claimed in claim 2, characterized in ii that k is set depending on the instantaneous relative speed.

4. The method as claim 1, characterized in that
   the digital filter (7) is a bandpass filter, in particular having constant filter coefficients that are predefined during operation.

5. The method as claimed in claim 1, characterized in that the word repetition rate of the digitized probe signal or of the digital demodulation signal lies in a range of 1 kHz to 200 MHz, in particular 2 MHz to 6 MHz.

6. The method as claimed in claim 1, characterized by the steps:
   applying an alternating magnetic field to the test object (8) in order to generate a resulting alternating magnetic field in the test object (8), the alternating magnetic field changing periodically with at least one predefined carrier frequency, such that the probe signal (US) has the at least one carrier frequency and is modulated in terms of its amplitude and/or phase depending on material properties of the test object, and
   digitally demodulating the digitized probe signal (USD) by multiplying the digitized probe signal (USD) by a digitized carrier signal having the at least one carrier frequency, in order to generate the digitized demodulation signal (UM) in the form of a sequence of digital words having the predefined word repetition rate.

7. A device for carrying out a method for testing the material of a test object (8) in nondestructive manner, said test object being moved relative to a probe (1) at a variable relative speed, including detecting a probe signal (US) by means of the probe (1), subjecting the probe signal US to analog-to-digital conversion in order to generate a digitized probe signal (USD) in the form of a sequence of digital words with a predefined, in particular constant, word repetition rate, n-stage decimation of the word repetition rate of the digitized probe signal (USD) or of a digital demodulation signal (UM) derived from the digitized probe signal, wherein the n-stage decimation is performed by means of n cascaded decimation stages (5_1 to 5_n), where n ≥2, selecting an output signal (UA_1 to UA_n) of one of the n decimation stages (5_1 to 5_n) depending on the instantaneous relative speed, and filtering the selected output signal by means of a digital filter (7), which is clocked with the word repetition rate of the selected output signal, wherein the device comprises;

the probe (1),
an analog-to-digital converter (3) designed for subjecting the probe Signal (US) to analog-to-digital conversion in order to generate the digitized probe signal,
the n cascade decimation stages (5_1 to 5_n),
selection means (6) designed for selecting the output signal (UA_1 to UA_n) of one of the n decimation stages (5_1 to 5_n) depending on the relative speed, and
the digital filter (7).

8. The device as claimed in claim 7, characterized in that
the probe (1) is a magnetic field probe designed, in particular, for detecting a magnetic field inductively or by using the Hall effect.

9. The device as claimed in claim 7, characterized by
magnetic field generating means designed for applying the alternating magnetic field to the test object, and
a digital demodulator (4) designed for digitally demodulating the digitized probe signal.

* * * * *